(12) United States Patent
Braun

(10) Patent No.: US 10,299,489 B2
(45) Date of Patent: May 28, 2019

(54) FLAVOUR MODULATION BY FERMENTING A MILK SOURCE FOR MULTI-FLAVOUR FORMATION WITH A COCKTAIL OF BACTERIAL STRAINS

(75) Inventor: Marcel Braun, Konolfingen (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/995,426

(22) PCT Filed: Dec. 20, 2011

(86) PCT No.: PCT/EP2011/073491
§ 371 (c)(1),
(2), (4) Date: Jun. 18, 2013

(87) PCT Pub. No.: WO2012/085011
PCT Pub. Date: Jun. 28, 2012

(65) Prior Publication Data
US 2013/0273200 A1 Oct. 17, 2013

(30) Foreign Application Priority Data

Dec. 20, 2010 (EP) ..................................... 10195855

(51) Int. Cl.
A23C 9/123 (2006.01)
A23C 9/13 (2006.01)
C12N 1/20 (2006.01)
C12R 1/46 (2006.01)
A23L 27/24 (2016.01)
A23L 29/00 (2016.01)

(52) U.S. Cl.
CPC .......... *A23C 9/1236* (2013.01); *A23C 9/1322* (2013.01); *A23L 27/25* (2016.08); *C12N 1/20* (2013.01); *C12R 1/46* (2013.01); *A23L 29/065* (2016.08); *A23Y 2240/41* (2013.01)

(58) Field of Classification Search
CPC ................................ A23C 9/1236; C12R 1/46
USPC ....................... 426/35, 43, 41, 61; 435/252.1
See application file for complete search history.

(56) References Cited

U.S. PATENT DOCUMENTS 4,889,736 A 12/1989 Doornbos et al.
7,674,489 B2 * 3/2010 Moran ................ A23C 9/1236
426/36

FOREIGN PATENT DOCUMENTS

WO 9933350 7/1999
WO 9933351 7/1999
WO 0200845 1/2002
WO 2008049581 5/2008

OTHER PUBLICATIONS

Ayad, E. H. E. et al. 1999. International Dairy Journal. 9: 725-735.*
A.N. Mutukumira et al., "Characterisation of a malty-compound producing *Lactococcus lactis* subsp. *lactis* biovar. *diacetylactis* C1 strain isolated from naturally fermented milk", Milchwissenschaft, vol. 64, No. 1, 2009, pp. 26-29—XP009147172.
J.A. Narvhus et al., "Production of fermented milk using a malty compound-producing strain of *Lactococcus lactis* subsp. *lactis* biovar. *diacetylactis*, isolated from Zimbabwean naturally fermented milk", International Journal of Food Microbiology, vol. 41, No. 1, May 5, 1998 pp. 73-80—XP002637587.
Hugenholtz et al. "Diacetyl production by different strains of *Lactococcus lactic* subsp. *lactis* var. *diacetylactic* and *Leuconostoc* spp." Applied Microbiology Biotechnology, vol. 38, Jan. 1, 1992, pp. 17-22—XP000606685.
Boumerdassi et al. "Effect of Citrate on Production of Diacetyl and Acetoin by *Lactococcus lactis* ssp. *lactis* CNRZ 483 Cultivated in the Presence of Oxygen" J Dairy Sci., vol. 80, 1997, pp. 634-639—XP027047845.

* cited by examiner

Primary Examiner — Hamid R Badr
(74) Attorney, Agent, or Firm — K&L Gates LLP

(57) ABSTRACT

A fermentation of a milk source to manufacture a fermented milk product with malty-chocolate-honey-butter-cream flavor and aroma. Fermentation is achieved by addition of adding a *Lactococcus lactis* subsp. *lactis diacetylactis* (CNCM No. I-4404) or a *Lactococcus lactis* subsp. *lactis diacetylactis* (CNCM No. I-4405) A further bacteria *Lactococcus lactis* subsp. *lactis* biovar is also added to the milk source. The milk source comprises amino acids and citrate prior to fermentation.

17 Claims, No Drawings

FLAVOUR MODULATION BY FERMENTING A MILK SOURCE FOR MULTI-FLAVOUR FORMATION WITH A COCKTAIL OF BACTERIAL STRAINS

CROSS REFERENCE TO RELATED APPLICATIONS

The present application is a National Stage of International Application No. PCT/EP2011/073491, filed on Dec. 20, 2011, which claims priority to European Patent Application No. 10195855.1, filed Dec. 20, 2010, the entire contents of which are being incorporated herein by reference.

FIELD OF INVENTION

The present invention relates to the generation of flavour and aroma in milk-based products. The generation of flavour and aroma in milk-based products is achieved using bacterial strains during fermentation of a milk source.

BACKGROUND OF THE INVENTION

Fermentation is a conversion of carbohydrates to organic acids or other compounds using bacterial strains.

Fermented milk products are major consumer products. Fermented milk products can be, for example, cheeses, buttermilks and yoghurts. Fermented milk products are manufactured by fermenting a milk source.

A milk source, for example milk, contains the carbohydrate lactose. During fermentation of the milk source the bacterial strains ferment the carbohydrate lactose to produce lactic acid. The production of lactic acid results in an acidification of the milk source during the manufacture of the fermented milk product. During fermentation of the milk source, other reactions may occur between other substances present in the milk source and the bacterial strains.

A fermentation of the milk source with bacterial strains is responsible for a generation of a flavour and aroma in the fermented milk products. Furthermore the fermentation of the milk source with the bacterial strains increases a shelf-life of the fermented milk products.

The bacterial strains used to ferment the milk source can be lactic acid bacterial strains. The lactic acid bacterial strains include *Lactobacillus, Leuconostoc, Pediococcus, Lactococcus* and *Streptococcus*; as well as the more peripheral *Aerococcus, Carnobacterium, Enterococcus, Oenococcus, Sporolactobacillus, Teragenococcus, Vagococcus* and *Weisella*; these lactic acid bacterial strains belong to the order Lactobacillales.

An international patent application publication No. WO 2008/049581 by the Applicant Nestec SA is titled "Taste and flavour modulation by biotransformation in milk products". The international patent application publication No. WO 2008/049581 discloses a method to promote a non-savoury flavour in a food product.

An international patent application publication No. WO 02/085131 by the Applicant New Zealand Dairy Board is titled "Method of preparing savoury-flavoured products by fermentation of proteins". The international patent application publication No. 02/085131 discloses a method for the manufacture of a savoury flavoured product from a source of protein using a combination of two distinct strains of bacteria. The source of protein may be a plant soy, wheat, rice, milk or whey. A first strain of bacteria is selected from the group *Macrococcus, Micrococcus, Entercoccus, Staphylococcus, Brevibacterium, Anthrobacter* and *Corynebacterium*, preferably *Macrococcus caseolyticus*. A second strain of bacteria is selected from the lactic acid bacteria—*Lactococcus, Lactobacillus, Pediococcus* or *Leuconostoc*. The savoury flavoured product may be combined with other ingredients to form products such as cheese, protein-water gels, yoghurts, creams, custards, sauces and confectionary products.

An international patent application publication No. WO 02/00845 by the Applicant Nizo Food Research is titled "Enhanced flavour production in or relating to food by cultivation of various food grade micro-organisms". The international patent application publication No. WO 02/00845 discloses new mixed cultures of two or more micro-organism strains wherein at least one of the micro-organism strains which are comprised in said mixed culture is individually selected on the basis of its ability to perform part of an enzymatic pathway, and said two or more selected micro-organism strains together form a complete pathway towards a desired flavour component. The mixed culture is a culture for the production of a fermented product, such as yogurt or cheese or sausage. Said two or more micro-organism strains are preferably co-cultivated. Particular and preferred embodiments are starter cultures for the manufacture of cheese. The mixed culture comprising a combination of various *Lactoccocus* strains and a combination of a *Brevibacterium* strain and a *Staphylococcus* strain, respectively.

An article by Monnet et al. in a Journal of Microbiological Methods 37 (1999) pp 183-185 is titled "An improved method for screening alpha-acetolactate producing mutants". The article by Monnet et al. discloses that a bacterial strain *Lactococcus Lactis* ssp. *Lactis* Biovar. *Diacetylactis* is used in the dairy industry to produce diacetyl. Diacetyl is a major flavour compound in cultured dairy products.

An article by Boumerdassi et al. in a Journal of Dairy Science Vol. 80 Issue 4 (1997) pp 634-639 is titled "Effect of citrate on production of diacetyl and acetoin by *Lactococcus Lactis* ssp. *Lactis* CNRZ 483 cultivated in the presence of oxygen". The article by Monnet et al. discloses the effects of trisoodium citrate addition on growth and formation of diacetyl and acetoin by *Lactococcus Lactis* ssp. *Lactis* CNRZ 483 in a whey based medium.

The article "Characterisation of a malty-compound producing *Lactococcus lactis* subsp. *lactis* biovar. *diacetylactis* C1 strain isolated from naturally fermented milk" by Mutukumira et al. (2009) Milchwissenschaft 64(1) pp. 26-29, relates to a strain that produced acceptable fermented milk to a sensory panel despite the presence of a slight malty flavour.

The article "Diacetyl production by different strains of *Lactococcus lactis* subsp. *lactis* biovar. *diacetylactis* and *Leuconostoc* spp." by Hugenholtz and Starrenburg (1992) Appl. Microbiol. Biotechnol 38, pp. 17-22, relates to the comparison of several strains for product formation from citrate in milk cultures.

Fermented milk products have a wide variety of flavours and aromas depending upon the milk source and the lactic acid bacterial strains used to ferment the milk source.

However, due to a number of the lactic acid bacterial strains and their interactions with individuals, a selection of certain lactic acid bacterial strains to produce certain flavours and aromas in the fermented milk products is not predictable.

There is a need to provide methods and lactic acid bacterial strains that are responsible for specific flavours and aromas in the fermented milk products.

Furthermore, artificial additives are negatively perceived by the consumer. There a need to provide flavour and aromas in a natural way that avoids artificial additives.

There is also a need to provide flavour and aromas which can be used in a wide range of foods.

There is thus a need to overcome the aforementioned problems in the art.

SUMMARY OF INVENTION

In a first aspect the present invention relates to a combination of lactic acid bacterium, *Lactococcus lactis* subsp. *lactis diacetylactis* (CNCM No. I-4404) with lactic acid bacterium, *Lactococcus lactis* subsp. *lactis* biovar *diacetylactis* (CNCM No. I-1962).

In a further aspect the present invention relates to combination of lactic acid bacterium, *Lactococcus lactis* subsp. *lactis diacetylactis* (CNCM No. I-4405) with lactic acid bacterium, *Lactococcus lactis* subsp. *lactis* biovar *diacetylactis* (CNCM No. I-1962).

In a further aspect the present invention relates to a use of the any one of the aforementioned combinations to impart at least a malty-chocolate-honey-butter-cream flavour and aroma to a milk source.

In a further aspect the present invention relates to a method for the manufacture of a fermented milk product. The fermented milk product has at least a malty-chocolate-honey-butter-cream flavour and aroma. The method comprises providing a milk source, then forming an amino acid supplemented milk source and adding trisodium citrate. A *Lactococcus lactis* subsp. *lactis diacetylactis* (CNCM No. I-4404) or a *Lactococcus lactis* subsp. *lactis diacetylactis* (CNCM No. I-4405) is then added. Then a *Lactococcus lactis* subsp. *lactis* biovar *diacetylactis* (CNCM No. I-1962) is added to form a mixture; finally the mixture is fermented to to manufacture the fermented milk product.

In a further aspect the present invention relates to a fermented milk product with at least a malty-chocolate-honey-butter-cream flavour and aroma obtainable by the method.

In a further aspect the present invention relates to a product for consumption by a mammal comprising the fermented milk product.

In a further aspect the present invention relates to a food product comprising a *Lactococcus lactis* subsp. *lactis diacetylactis* (CNCM No. I-4404) and a *Lactococcus lactis* subsp. *lactis* biovar *diacetylactis* (CNCM No. I-1962) or a food product comprising a *Lactococcus lactis* subsp. *lactis diacetylactis* (CNCM No. I-4405) and a *Lactococcus lactis* subsp. *lactis* biovar *diacetylactis* (CNCM No. I-1962) wherein the food product comprises at least one of diacetyl, acetoin and 4-dihydroxy-3,4-dimethyl-2,5-hexanedione and at least one of 2-methylpropanal, 2/3-methylbutanal, phenylacetaldehyde and 2/3-methylbutanol.

The present inventors were surprised to find that such a unique combination of bacterial strains were responsible for providing such a flavour and aroma profile to fermented milk products.

DETAILED DESCRIPTION OF INVENTION

For a complete understanding of the present invention and the advantages thereof, reference is made to the following detailed description of the invention.

It should be appreciated that various aspects of the present invention are merely illustrative of the specific ways to make and use the present invention.

The various aspects of the present invention can be combined with other aspects of the present invention and do not limit the scope of the invention when taken into consideration with the claims and the following detailed description.

The present invention concerns fermented milk products. The fermented milk products are manufactured by a fermentation of a milk source with a lactic acid bacteria cocktail to provide flavour and aroma to the fermented milk products.

The lactic acid bacteria cocktail can be a combination of lactic acid bacterium, *Lactococcus lactis* subsp. *lactis diacetylactis* (CNCM No. I-4404) with lactic acid bacterium, *Lactococcus lactis* subsp. *lactis* biovar *diacetylactis* (CNCM No. I-1962).

The lactic acid bacteria cocktail can also be a combination of lactic acid bacterium, *Lactococcus lactis* subsp. *lactis diacetylactis* (CNCM No. I-4405) with lactic acid bacterium, *Lactococcus lactis* subsp. *lactis* biovar *diacetylactis* (CNCM No. I-1962).

The lactic acid bacterium, *Lactococcus lactis* subsp. *lactis diacetylactis* (CNCM No. I-4404) and the *Lactococcus lactis* subsp. *lactis diacetylactis* (CNCM No. I-4405) were deposited on 25 Nov. 2010 with the Institut Pasteur—Collection Nationale de Cultures de Mico-organisme (CNCM).

The lactic acid bacterium, *Lactococcus lactis* subsp. *lactis* biovar *diacetylactis* (CNCM No. I-1962) was deposited in 1997 with the Institut Pasteur—Collection Nationale de Cultures de Mico-organisme (CNCM).

The milk source can be any type of milk; such as cow milk, sheep milk, goat milk and buffalo milk or any mixtures thereof. The milk source may be UHT-treated milk, pasteurised milk or non-pasteurised milk. The milk source may be full fat milk, a skimmed milk or semi-skimmed milk. Furthermore the milk source may be a fresh milk, recombined milk and milk containing vegetable fat and any mixtures thereof.

A conversion of amino acids into volatile flavour and aroma compounds plays an important role in food technology. The conversion of amino acids into volatile flavour and aroma compounds can be achieved by the lactic acid bacteria cocktail. Therefore there is a need to supplement the milk source with amino acids. That is to say that amino acids are supplemented to the milk source in addition to any amino acids that are naturally present in the milk source. In order to supplement the milk source at least one of an amino acid(s), a protease or a peptidase or any mixture thereof is added to the milk source. The amino acids are at least one of L-phenylalanine, L-leucine, L-isoleucine, L-valine. It is preferable that the peptidases is an exo-peptidases applied as an enzyme preparation (for example produced by *Aspergillus oryzae, Aspergillus sojae, Rhizophus oryzae, Bacillus subtilis, Ananas comosus*) or as microbial strains with exo-proteolytic activity (for example *L. helveticus, S. thermophilus, L. plantarum, L. lactis* subspecies). The peptidases or proteases release amino acid(s) such as L-phenylalanine, L-leucine, L-isoleucine, L-valine by an interaction with peptides and proteins naturally present in the milk source.

The amino acids are converted into volatile flavour and aroma compounds which are honey-like, malt-like or chocolate-like volatile flavour and aroma compounds as discussed below.

The peptidases or proteases can be added without the amino acid(s) or with the amino acids. The at least one of the amino acid(s), the protease or the peptidase or any mixture thereof are added to the milk source in amount of 0.01 to 5 wt %, preferably 0.01-2 wt %, more preferably in an amount of 0.03-1.0 wt %, most preferably 0.05-0.3 wt %.

A conversion of citrate into volatile flavour and aroma compounds also plays an important role in food technology. The conversion of citrate into volatile flavour and aroma compounds can be achieved by the lactic acid bacteria cocktail. Therefore there is a need to supplement the milk source with a citrate compound e.g. trisodium citrate.

The citrate is converted into volatile flavour and aroma compounds during fermentation. The volatile flavour and aroma compounds have at least a cream like flavour and aroma as discussed below.

The trisodium citrate is added to the milk source in an amount of 0.01 to 5 wt %, preferably 0.01-2 wt %, more preferably in an amount of 0.03-1.0 wt %, most preferably 0.05-0.3 wt %.

Lipase can also be added to the milk source prior to or during fermentation to produce an enhanced flavour and aroma in the fermented milk products. Lipase hydrolyses fats in the milk source to form for example diglycerides, monoglycerides and free fatty acids or any mixtures thereof. The diglycerides, monoglycerides and free fatty acids impart a cream-like flavour to the fermented milk product. Therefore the use of lipase enhances the cream like flavour in the fermented milk product.

Lactase can also be added to the milk source prior to or during fermentation to produce an enhanced flavour and aroma in the fermented milk products. Lactase hydrolyses the disaccharide lactose in the milk source into galactose and glucose. Glucose and galactose are used as flavour precursors for caramel-like and sweetened condensed milk-like flavour formation.

If the milk source is non-pasteurised, the milk source or the supplemented milk source may be pasteurised, subjected to ultra-high temperature treatment (UHT-milk) or sterilised under conditions known in the art. The pasteurisation, ultra-high temperature treatment and sterilisation is carried out in a temperature range of 70° C. to 150° C. for a time of between 2 s to 20 min. Alternatively, the milk source may be heat-treated prior to being the supplemented milk source.

Once the milk source has been supplemented with the amino acids the trisodium citrate is added. Then the lactic acid bacteria cocktail is added to form a mixture. The order in which these components are added is not important, it is important that all of the components are present in the mixture.

The mixture is then fermented to manufacture the fermented milk product. The fermented milk product surprisingly has a malty-chocolate-honey-butter-cream flavour and aroma. The fermentation is allowed to take place for between 6 and 24 hours at a temperature of approximately 30° C.

Fermentation improving cofactors such as alpha-ketoglutarate, manganese or magnesium salts may also be added prior to the fermentation or during the fermentation step.

Depending upon the milk source it is to be appreciated that the fermented milk product with the malty-chocolate-honey-butter-cream flavour and aroma can be in the form of a slurry (yogurt like) or a liquid.

The fermented milk product with the malty-chocolate-honey-butter-cream flavour and aroma can be dried or concentrated. The fermented milk product with the malty-chocolate-honey-butter-cream flavour and aroma can be dried, preferably by spray-drying and then converted into a powder.

The fermented milk product with the malty-chocolate-honey-butter-cream flavour and aroma can have applications in food products and during a manufacture of food products. For example, the powder with the malty-chocolate-honey-butter-cream flavour and aroma can have applications in the beverage industry to impart the malty-chocolate-honey-butter-cream flavour and aroma to beverages. Furthermore, the powder with the malty-chocolate-honey-butter-cream flavour and aroma can have applications in the food industry to impart the malty-chocolate-honey-butter-cream flavour and aroma to foodstuffs.

EXAMPLES

The manufactured fermented milk product with the malty-chocolate-honey-butter-cream flavour and aroma were analysed by an electronic nose based on mass spectrometry and gas chromatography coupled to mass spectrometry (GC-MS).

Analysis with electronic nose based on mass spectrometry is a direct analysis method wherein the fermented milk product is placed directly into the ion source without the need for separation procedures and is therefore time-saving. A determination of volatiles from such a resultant mass spectra contains limited information for the identification of aroma components. Unequivocal identification of the single compounds present is not possible without prior separation and selective fragmentation i.e. GC-MS.

Gas chromatography coupled to mass spectrometry (GC-MS) provides the necessary separation and detection of volatiles. GC-MS is used for obtaining MS fragments belonging to a specific aroma component. The unambiguous identification of the molecules by GC-MS in combination with olfactometry analysis is mandatory for analysing volatiles with a specific odour.

Commonly used extraction methods for the isolation of volatiles from fermented milk products are vacuum distillation followed by solvent extraction, purge and trap (PT) and headspace techniques such as headspace solid-phase micro extraction (HS-SPME). The purge and trap (PT) and headspace techniques methods identify volatiles with different yield performances, but with comparable reproducibility. PT appeared to be a more sensitive whereas SPME is a more rapid and less expensive technique.

The reagents where used, were used as received without prior treatment unless otherwise stated.

Example 1

A—Reactivation of Lactic Acid Bacterium—Bacterial Cocktail

The *Lactococcus lactis* subsp. *lactis diacetylactis* (CNCM No. I-4404) in ampoules was reactivated with 1 ml reconstituted milk under sterile conditions, transferred into sterile glass tubes containing 9 ml reconstituted milk and incubated aerobically at 30° C. for 24 h in the dark. The bacteria were then stored at 6° C. for two weeks and subsequently inoculated at 0.5% ((v/v) 0.05/10 ml medium) in a culture. The culture was M17x (M17 Terzaghi Bouillon, Merck 1.15029 and 5 g/l glucose (Merck 8342). After the growth phase (3 days) the flasks were stored at 6° C. to form the reactivated lactic acid bacterium.

The lactic acid bacterium, *Lactococcus lactis* subsp. *lactis* biovar *diacetylactis* (CNCM No. I-1962) in ampoules was reactivated with 1 ml reconstituted milk under sterile conditions, transferred in sterile glass tubes containing 9 ml reconstituted milk and incubated aerobically at 30° C. for 24 h in the dark. The lactic acid bacterium, *Lactococcus lactis* subsp. *lactis* biovar *diacetylactis* (CNCM No. I-1962) were stored at 6° C. for two weeks and subsequently inoculated at 0.5% ((v/v) 0.05/10 ml medium) in a culture. The culture was M17x (M17 Terzaghi Bouillon, Merck 1.15029 and 5 g/l glucose (Merck 8342). After the growth phase (3 days) the flasks were stored at 6° C. to form a reactivated lactic acid bacterium.

The lactic acid bacteria cocktail was prepared by mixing the above two reactivated lactic acid bacterium in a 1:1 ratio.

Alternatively the culture can be skimmed milk.

B—Milk Source Supplementation with Trisodium Citrate and Amino Acids

A 100 mM trisodium citrate solution in water was manufactured. The trisodium citrate solution was filtrated through a pore size of 0.45 μm (Schleicher & Schuell, Whatmann, FP 30/0.45 μm, 7 bar max. CA-S).

An amino acid solution of 100 mM concentration was manufactured. L-phenylalanine (Fluka, Buchs, Switzerland) (1.65 g/100 ml), L-leucine (Merck, Darmstadt, Germany) (1.31 g/100 ml), L-isoleucine (Merck, Darmstadt, Germany) (1.31 g/100 ml), L-valine (Merck, Darmstadt, Germany) (1.17 g/100 ml) was dissolved in sterile water. The amino acid solution was filtrated through a pore size of 0.45 μm (Schleicher & Schuell, Whatmann, FP 30/0.45 μm, 7 bar max. CA-S).

To 4.5 ml UHT-milk, 250 μl of the trisodium citrate solution was added and 250 μl of the amino acid solution was added.

C—Fermentation

Fermentation in UHT-milk was performed by two approaches (I-II).

I: Index (Inside needle dynamic extraction; Hamilton) headspace sampling of volatile compound fragments in non-supplemented UHT-milk.

II: Tenax (accumulation adsorbens, Marin-Epagnier, Switzerland) headspace sampling of volatile compounds in supplemented milk source UHT-milk.

An aliquot of 50 μl of the lactic acid bacteria cocktail was transferred in 5 ml supplemented milk source UHT milk (1% inoculation) under sterile conditions and incubated at 30° C. aerobically for 22 hours in the dark.

An addition of 2.8 g NaCl into the headspace vials helped to expel the volatiles from the fermented milk product into the headspace to get more intense release of the volatiles.

An electronic nose detected the volatile compound fragments at a range of m/z 40-100 for the experiment with non-supplemented UHT-milk (i.e. no trisodium citrate) and at m/z 10-160 for the experiment with supplemented UHT-milk (i.e. with trisodium citrate).

Principle component analysis (PCA) was calculated using the software program "The Unscrambler" (version 9.7). The results were calculated with logarithmised raw data and exclusion of the water and milk blanks. The calculations were done with all variables (MS fragments) included to group the strains in relation to similar MS-fragment patterns and abundance of compounds.

D—Electronic Nose Measurements

Analysis of the fermented milk product by the electronic nose measurements in supplemented milk source UHT-milk was conducted. Tenax headspace measurement with supplemented UHT-milk. GC-MS fragments [M]$^+$ were 27, 29, 43, 45, 60, 70, 86, 87, 88 and 135.

E—Sensory Assessment of Fermented Milk Product

After fermentation the glass vials were kept closed until sensory evaluation started. Seven persons attended the sensory assessment of the fermented milk product. The sensory assessment was based on the following attributes, scoring is noted with a X. A blank sample (incubated milk) was given as a reference. In order to test the influence of the trisodium citrate samples were also prepared without the trisodium citrate (addition of sterile water only) and presented to the panel. The results are shown below, wherein an X indicated a sensory perception of the fermented milk product to the panelist.

| | |
|---|---|
| Buttery | XXXX |
| Bitter/-almond | X |
| Flower-like | X |
| Bread-like | X |
| Creamy | XXX |
| Caramel | — |
| Strawberry | — |
| Fresh | — |
| Fruity | — |
| Yeast | X |
| Honey | XXX |
| Yoghurt | — |
| Cheesy | — |
| Milky | — |
| Malty | XXX |
| Almond | XX |
| Nutty | X |
| Paper-like | — |
| Sweet | X |
| Acidic | X |
| Salty | — |
| Chocolate | XXX |

The results of the sensory assessment of the fermented milk product demonstrate that the fermented milk product has a malty-chocolate-honey-butter-cream flavour and aroma.

The malty flavour and aroma can be attributed to the presence of 2-methylpropanal, 2-methylbutanal, 3-methylbutanal, phenylacetaldehyde, 2-methylbutanol and 3-methylbutanol as determined by the electronic nose measurements. The buttery/creamy flavour and aroma is due to the presence of diacetyl, acetoin and 3,4-dihydroxy-3,4-dimethyl-2,5-hexanedione. The combination of the bacterial strains is responsible for the overall flavour and aroma in the fermented milk product.

Example 2

A—Reactivation of Lactic Acid Bacterium—Bacterial Cocktail

The *Lactococcus lactis* subsp. *lactis diacetylactis* (CNCM No. I-4405) in ampoules was reactivated with 1 ml reconstituted milk under sterile conditions, transferred into sterile glass tubes containing 9 ml reconstituted milk and incubated aerobically at 30° C. for 24 h in the dark. The bacteria were then stored at 6° C. for two weeks and subsequently inoculated at 0.5% ((v/v) 0.05/10 ml medium) in a culture. The culture was M17x (M17 Terzaghi Bouillon, Merck 1.15029 and 5 g/l glucose (Merck 8342). After the growth phase (3 days) the flasks were stored at 6° C. to form the reactivated lactic acid bacterium.

The lactic acid bacterium, Lactococcus lactis subsp. lactis biovar diacetylactis (CNCM No. I-1962) in ampoules was reactivated with 1 ml reconstituted milk under sterile conditions, transferred in sterile glass tubes containing 9 ml reconstituted milk and incubated aerobically at 30° C. for 24 h in the dark. The lactic acid bacterium, Lactococcus lactis subsp. lactis biovar diacetylactis (CNCM No. I-1962) were stored at 6° C. for two weeks and subsequently inoculated at 0.5% ((v/v) 0.05/10 ml medium) in a culture. The culture was M17x (M17 Terzaghi Bouillon, Merck 1.15029 and 5 g/l glucose (Merck 8342). After the growth phase (3 days) the flasks were stored at 6° C. to form a reactivated lactic acid bacterium.

Alternatively the culture can be skimmed milk.

The lactic acid bacteria cocktail was prepared by mixing the above two reactivated lactic acid bacterium in a 1:1 ratio.

B—Milk Source Supplementation with Trisodium Citrate and Amino Acids

A 100 mM trisodium citrate solution in water was manufactured. The trisodium citrate solution was filtrated through a pore size of 0.45 µm (Schleicher & Schuell, Whatmann, FP 30/0.45 µm, 7 bar max. CA-S).

An amino acid solution of 100 mM concentration was manufactured. L-phenylalanine (Fluka, Buchs, Switzerland) (1.65 g/100 ml), L-leucine (Merck, Darmstadt, Germany) (1.31 g/100 ml), L-isoleucine (Merck, Darmstadt, Germany) (1.31 g/100 ml), L-valine (Merck, Darmstadt, Germany) (1.17 g/100 ml) was dissolved in sterile water. The amino acid solution was filtrated through a pore size of 0.45 µm (Schleicher & Schuell, Whatmann, FP 30/0.45 µm, 7 bar max. CA-S).

To 4.5 ml UHT-milk, 250 µl of the trisodium citrate solution was added and 250 µl of the amino acid solution was added.

C—Fermentation

Fermentation in UHT-milk was performed by two approaches (I-II).

I: Index (Inside needle dynamic extraction; Hamilton) headspace sampling of volatile compound fragments in non-supplemented UHT-milk.

II: Tenax (accumulation adsorbens, Marin-Epagnier, Switzerland) headspace sampling of volatile compounds in supplemented UHT-milk.

An aliquot of 50 µl of the lactic acid bacteria cocktail was transferred in 5 ml supplemented milk source UHT milk (1% inoculation) under sterile conditions and incubated at 30° C. aerobically for 22 hours in the dark.

An addition of 2.8 g NaCl into the headspace vials helped to expel the volatiles from the fermented milk product into the headspace to get more intense release of the volatiles.

An electronic nose detected the volatile compound fragments at a range of m/z 40-100 for the experiment with non-supplemented UHT-milk and at m/z 10-160 for the experiment with supplemented UHT-milk.

Principle component analysis (PCA) was calculated using the software program "The Unscrambler" (version 9.7). The results were calculated with logarithmised raw data and exclusion of the water and milk blanks. The calculations were done with all variables (MS fragments) included to group the strains in relation to similar MS-fragment patterns and abundance of compounds.

D—Electronic Nose Measurements

Analysis of the fermented milk product by the electronic nose measurements in supplemented milk source UHT-milk was conducted. II: Tenax headspace measurement with supplemented UHT-milk. GC-MS fragments [M]$^+$ were 43, 55, 71, 77, 60, 88, 89, 99, 114, 120 and 131.

E—Sensory Assessment of Fermented Milk Product

After bacterial fermentation the glass vials were kept close until sensory evaluation started. Seven persons attended the sensory assessment of the fermented milk product. The sensory evaluation was a taste evaluation in order to gain information on the in mouth—effect and taste of the obtained fermented milk products.

In each case the samples were pasteurised (85° C. for 15 min in a water bath) and diluted to 1% in UHT milk (at a temperature 20-25° C.). The results shown in the table below detail the inferences of the panelists.

| Panellist | Blank Incubated UHT-milk | Fermented milk product |
|---|---|---|
| 1 | Slightly milky | malty-chocolate-honey-butter-cream |
| 2 | Milky, UHT-milk | malty-chocolate-honey-cream |
| 3 | Slightly Sour | malty-honey-butter-cream |
| 4 | Milky, Slight | malty-chocolate-honey-butter-cream |
| 5 | Milky | malty-chocolate-honey-butter |
| 6 | Milky, Fatty | malty-honey-butter-cream |
| 7 | Milk powder, Sweet | malty-chocolate-honey-butter-cream |

The results of the sensory assessment of fermented milk product demonstrate that the fermented milk product has a predominantly malty-chocolate-honey-butter-cream like flavour and aroma.

The malty flavour and aroma can be attributed to the presence of 2-methylpropanal, 2-methylbutanal, 3-methylbutanal, phenylacetaldehyde, 2-methylbutanol and 3-methylbutanol as determined by the electronic nose measurements. The buttery/creamy flavour and aroma is mainly due to the presence of diacetyl, acetoin and 3,4-dihydroxy-3,4-dimethyl-2,5-hexanedione. The combination of the bacterial strains is responsible for the overall flavour and aroma in the fermented milk product.

Example 3

A—Reactivation of Lactic Acid Bacterium—Bacterial Cocktail

See example 2

B—Milk Source Supplementation with Trisodium Citrate and Amino Acids

A 100 mM trisodium citrate solution in water was manufactured. The trisodium citrate solution was filtrated through a pore size of 0.45 µm (Schleicher & Schuell, Whatmann, FP 30/0.45 µm, 7 bar max. CA-S).

An amino acid solution of 100 mM concentration was manufactured. The amino acid solution consisted of L-phenylalanine, L-isoleucine and L-valine. The solution was prepared by dissolving the amino acids in sterile water. The amino acid solution was filtrated through a pore size of 0.45 µm (Schleicher & Schuell, Whatmann, FP 30/0.45 µm, 7 bar max. CA-S).

To 4.5 ml UHT-milk, 250 µl of the trisodium citrate solution was added and 250 µl of the amino acid solution was added.

C—Fermentation

Fermentation in UHT-milk was performed by two approaches (I-II).

I: Index (Inside needle dynamic extraction; Hamilton) headspace sampling of volatile compound fragments in non-supplemented UHT-milk.

II: Tenax (accumulation adsorbens, Marin-Epagnier, Switzerland) headspace sampling of volatile compounds in supplemented UHT-milk.

An aliquot of 50 µl of the lactic acid bacteria cocktail was transferred in 5 ml supplemented milk source UHT milk (1% inoculation) under sterile conditions and incubated at 30° C. aerobically for 18 hours in the dark.

An addition of 2.8 g NaCl into the headspace vials helped to expel the volatiles from the fermented milk product into the headspace to get more intense release of the volatiles.

An electronic nose detected the volatile compound fragments at a range of m/z 40-100 for the experiment with non-supplemented UHT-milk and at m/z 10-160 for the experiment with supplemented UHT-milk.

Principle component analysis (PCA) was calculated using the software program "The Unscrambler" (version 9.7). The results were calculated with logarithmised raw data and exclusion of the water and milk blanks. The calculations were done with all variables (MS fragments) included to group the strains in relation to similar MS-fragment patterns and abundance of compounds.

D—Electronic Nose Measurements

Analysis of the fermented milk product by the electronic nose measurements in supplemented milk source UHT-milk was conducted. II: Tenax headspace measurement with supplemented UHT-milk. GC-MS fragments $[M]^+$ were 43, 55, 71, 77, 60, 88, 89, 99, 114, 120 and 131.

E—Sensory Assessment of Fermented Milk Product

After bacterial fermentation the glass vials were kept close until sensory evaluation started. Seven persons attended the sensory assessment of the fermented milk product. The sensory evaluation was a taste evaluation in order to gain information on the in mouth—effect and taste of the obtained fermented milk products.

In each case the samples were pasteurised (85° C. for 15 min in a water bath) and diluted to 1% in UHT milk (at a temperature 20-25° C.). The results shown in the table below detail the inferences of the panelists.

| Panellist | Blank Incubated UHT-milk | Fermented milk product |
|---|---|---|
| 1 | Slightly milky | malty-chocolate-honey-butter-cream |
| 2 | Milky, UHT-milk | chocolate-honey-cream |
| 3 | Slightly Sour | malty-honey-butter-cream |
| 4 | Milky, Slight | malty-chocolate-honey-butter-cream |
| 5 | Milky | malty-chocolate-honey-butter |
| 6 | Milky, Fatty | malty-honey-butter-cream |
| 7 | Milk powder, Sweet | malty-chocolate-honey-butter-cream |

The results of the sensory assessment of fermented milk product demonstrate that the fermented milk product has a predominantly malty-chocolate-honey-butter-cream like flavour and aroma.

The malty flavour and aroma can be attributed to the presence of 2-methylpropanal, 2-methylbutanal, 3-methylbutanal, phenylacetaldehyde, 2-methylbutanol and 3-methylbutanol as determined by the electronic nose measurements. The buttery/creamy flavour and aroma is due to the presence of diacetyl, acetoin and 3,4-dihydroxy-3,4-dimethyl-2,5-hexanedione. The combination of the bacterial strains is responsible for the overall flavour and aroma in the fermented milk product.

Having thus described the present invention in detail, it is to be understood that the detailed description is not intended to limit the scope of the invention thereof.

What is desired to be protected by Letters Patent is set forth in the following claims:

1. A method for imparting malty and creamy flavour and aroma to a milk source, the method comprising:
    adding to the milk source a combination selected from the group consisting of (i) *Lactococcus lactis* subsp. *lactis* biovar. *diacetylactis* (CNCM No. I-4404) with *Lactococcus lactis* subsp. *lactis* biovar. *diacetylactis* (CNCM No. I-1962) and (ii) *Lactococcus lactis* subsp. *lactis* biovar. *diacetylactis* (CNCM No. I-4405) with *Lactococcus lactis* subsp. *lactis* biovar. *diacetylactis* (CNCM No. I-1962), and the combination produces phenylacetaldehyde, 2-methylbutanol, and 3,4-dihydroxy-3,4-dimethyl-2,5-hexanedione in the milk source to form a fermented milk product comprising malty and creamy flavour and aroma.

2. A method for manufacture of a fermented milk product, the method comprising:
    providing a milk source;
    forming an amino acid supplemented milk source and optionally adding citrate;
    adding a *Lactococcus lactis* subsp. *lactis* biovar. *diacetylactis* (CNCM No. I-4404) or a *Lactococcus lactis* subsp. *lactis* biovar. *diacetylactis* (CNCM No. I-4405);
    adding a *Lactococcus lactis* subsp. *lactis* biovar. *diacetylactis* (CNCM No. I-1962) to form a mixture; and
    fermenting the mixture to produce phenylacetaldehyde, 2-methylbutanol, and 3,4-dihydroxy-3,4-dimethyl-2,5-hexanedione and manufacture the fermented milk product, the fermented milk product comprising malty and creamy flavour and aroma.

3. The method according to claim 2, wherein forming the amino acid supplemented milk source comprises addition of at least one component selected from the group consisting of an amino acid, a protease and a peptidase to the milk source.

4. The method according to claim 3, wherein the amino acid is selected from the group consisting of L-phenylalanine, L-leucine, L-isoleucine, L-valine, and mixtures thereof.

5. The method according to claim 2 comprising concentrating the fermented milk product to form a fermented milk product concentrate.

6. The method according to claim 2 comprising drying the fermented milk product to form a powder.

7. The method according to claim 2, wherein the milk source is selected from the group consisting of a full fat milk, skimmed milk, semi-skimmed milk, fresh milk, recombined milk, cream, buttermilk, whey and milk containing vegetable fat.

8. The method according to claim 2 comprising addition of at least one of a lipase enzyme and a lactase enzyme to the milk source.

9. The method according to claim 2 comprising adding a fermentation co-factor to the milk source.

10. The method according to claim 1, comprising adding citrate and an amino acid to the milk source before fermenting, wherein a total amount of the citrate and the amino acid is between 0.01 to 5 wt % with respect to the milk source.

11. A food product comprising:
a combination selected from the group consisting of (i) *Lactococcus lactis* subsp. *lactis* biovar. *diacetylactis* (CNCM No. I-4404) with *Lactococcus lactis* subsp. *lactis* biovar. *diacetylactis* (CNCM No. I-1962) and (ii) *Lactococcus lactis* subsp. *lactis* biovar. *diacetylactis* (CNCM No. I-4405) with *Lactococcus lactis* subsp. *lactis* biovar. *diacetylactis* (CNCM No. I-1962);
3,4-dihydroxy-3,4-dimethyl-2,5-hexanedione;
phenylacetaldehyde; and
2-methylbutanol,
wherein the food product has malty and creamy flavour and aroma.

12. The method according to claim 2, wherein the milk source is selected from the group consisting of cow milk, sheep milk, goat milk, buffalo milk and mixtures thereof.

13. The method according to claim 2, wherein the milk source is selected from the group consisting of ultra-high temperature treatment (UHT)-treated milk, pasteurized milk, non-pasteurized milk, and mixtures thereof.

14. The method according to claim 2, comprising adding to the mixture an exo-peptidase from at least one of *Aspergillus oryzae, Aspergillus sojae, Rhizophus oryzae, Bacillus subtilis, Ananas comosus, Lactobacillus helveticus, Streptococcus thermophilus*, or *Lactobacillus plantarum*.

15. The method according to claim 2, wherein at least a portion of the citrate is added to the milk source as trisodium citrate in an amount that is 0.01 to 5.0 wt. % of the milk source.

16. The method according to claim 2, comprising addition of both a lipase enzyme and a lactase enzyme to the milk source.

17. The method according to claim 9, wherein the fermentation co-factor is selected from the group consisting of alpha-ketoglutarate, manganese, magnesium salts and mixtures thereof.

* * * * *